United States Patent
Kuroda et al.

(10) Patent No.: US 6,649,757 B2
(45) Date of Patent: Nov. 18, 2003

(54) PROCESS FOR PRODUCING LAUROLACTAM FROM CYCLODODECANONE

(75) Inventors: Nobuyuki Kuroda, Ube (JP); Joji Kawai, Ube (JP); Hideo Shimomura, Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 10/345,548

(22) Filed: Jan. 16, 2003

(65) Prior Publication Data

US 2003/0139596 A1 Jul. 24, 2003

(30) Foreign Application Priority Data

| Jan. 16, 2002 | (JP) | 2002-007549 |
| Feb. 28, 2002 | (JP) | 2002-053903 |
| Feb. 28, 2002 | (JP) | 2002-053931 |
| Mar. 29, 2002 | (JP) | 2002-095024 |
| Jul. 18, 2002 | (JP) | 2002-209935 |

(51) Int. Cl.$^7$ .................................................. C07D 225/02
(52) U.S. Cl. .................................................... 540/464
(58) Field of Search .......................................... 540/464

(56) References Cited

U.S. PATENT DOCUMENTS 5,245,029 A  9/1993  Inaba et al. ................. 540/540

FOREIGN PATENT DOCUMENTS

| CH | 532 053 A | 12/1972 |
| EP | 0 487 090 A | 5/1992 |
| EP | 0 785 188 A | 7/1997 |
| JP | B43 12153 | 5/1968 |
| JP | B48 10475 | 4/1973 |

OTHER PUBLICATIONS

Ritz, J. et al., "Caprolactam" Ullmann's Encyclopedia of Industrial Chemistry. Cancer Chemotherapy to Ceramic Colorants, Weinheim, VCH Verlag, DE, vol. 15, 1986, pp. 31–50, XP002909167.

Primary Examiner—Bruck Kifle
(74) Attorney, Agent, or Firm—Piper Rudnick LLP

(57) ABSTRACT

Laurolactam having high quality is produced by reacting cyclododecanone with a hydroxylamine salt of a mineral acid, and converting the resultant cyclododecanoneoxime to laurolactam through the Beckmann rearrangement reaction, wherein a content of each of oxygen atom-containing $C_{12}$ organic compounds, for example, cyclododecenone or epoxycyclododecane, and cycloaliphatic unsaturated $C_{12}$ hydrocarbon compounds, contained, as an impurity, in the staring cyclododecanone material, is controlled to 1,000 ppm or less.

9 Claims, No Drawings

PROCESS FOR PRODUCING LAUROLACTAM FROM CYCLODODECANONE

BACKGROUND OF THE INVENTION

(1) Field of the Invention

The present invention relates to a process for producing laurolactam from cyclododecanone. More particularly, the present invention relates to a process for producing laurolactam having a high degree of purity from cyclododecanone used as a starting material.

Laurolactam is useful as a material for producing synthetic resins such as polyamide resins.

(2) Description of the Related Art

As a conventional method of producing laurolactam, a method in which cyclodododecanone, having been prepared by oxidizing cyclododecane with molecular oxygen-containing gas and dehydrogenating the resultant cyclydodecanol, is reacted, as a starting material, with a hydroxylamine mineral acid salt to prepare cyclododecanoneoxime and the resultant cyclododecanoneoxime is subjected to the Beckmann rearrangement reaction to produce the target laurolactam, is known. As another method of producing cyclododecanone, a method in which epoxycyclododecadiene is reduced with hydrogen and the resultant epoxycyclododecane is isomerized with an alkali metal salt, etc., to prepare the target cyclododecanone, is known.

In the method of producing cyclododecanone using, as a starting material, epoxycyclododecadiene, in the case where the reduction of epoxycyclododecadiene with hydrogen is incompletely carried out, the resultant epoxycyclododecane contains an impurity consisting of epoxycyclododecene and the epoxycyclododecene is converted to cyclododecenone by the isomerization reaction. The cyclododecenone is an impurity which is difficult to remove, as an impurity, from the target cyclododecanone by distillation. Also, in the case where cyclododecanol is dehydrogenated, cyclododecenone may be produced as a by-product, when the reaction conditions are inappropriate.

Further it is known that, in the reaction for isomerizing epoxycyclododecane in the presence of an alkali metal salt, undesired compounds having one or more double bonds between carbon atoms, such as cyclododecadiene, cyclododecene and cyclododecenol are produced as by-products.

Further, it is known that, in the method in which cyclododecanone, having been prepared by oxidizing cyclododecane with a molecular oxygen-containing gas and dehydrogenating the resultant cyclododecanol, is employed as a starting material for the production of laurolactam, the cyclododecanone produced by the oxidation of cyclododecane is further oxidized to produce 1,2-diketone compound and α-hydroxyketone compound, and the α-hydroxyketone compound is further converted to 1,2-diketone compound (cyclododecane-1,2-dione) during the dehydrogenation reaction procedure for cyclododecanol.

Where cyclododecanone is produced from a starting material consisting of epoxycyclododecadiene, the 1,2-diketone compound is not directly produced. However, when cyclododecanone is handled at a temperature of 100° C. or more in the presence of a molecular oxygen-containing gas, the 1,2-diketone compound is produced. In this case, the 1,2-diketone compound is an impurity which is difficult to separate from cyclododecanone by distillation.

Furthermore, it is known that in a method for preparing a mixture of cyclododecanol with cyclododecanone, by oxidizing cyclododecane with a molecular oxygen-containing gas, epoxycyclododecane is produced as a by-product, and in the distillation refining procedure for isolating refined cyclododecanone from the mixture, the distilled cyclododecanone fraction contains the above-mentioned epoxycyclododecane as an impurity.

Still further, it is known that in the case where epoxycyclododecadiene is used as a starting material for the production of cyclododecanone, and subjected to an isomerization reaction thereof, a small amount of cycloundecylcarboxyaldehyde is produced as a by-product. The cycloundecylcarboxyaldehyde is an impurity which is difficult to separate from cyclododecanone by distillation.

Also, in the method of preparing a mixture of cyclododecanol with cyclododecanone by oxidizing cyclododecane with a molecular oxygen-containing gas, undecylaldehyde is produced as a by-product and is contained in refined cyclododecanone fraction obtained by distillation of the mixture.

When the aldehyde compound-containing cyclododecanone is subjected to the cyclododecanoneoxime-preparing procedure and then to the Beckmann rearrangement reaction, the aldehyde compound is converted to a corresponding amide compound and the amide compound is kept contained in the target laurolactam. The contained amide compound causes the quality of the resultant laurolactam to be decreased.

Furthermore, it is known from the disclosure of Japanese Examined Patent Publication No. 43-12153 and No. 48-10475 that, in the production of laurolactam by converting cyclododecanone to an oxime thereof and subjecting the resultant cyclododecanoneoxime to the Beckmann rearrangement reaction, if the temperature of the Beckmann rearrangement reaction is too high, the cyclododecanoneoxime is decomposed due to the poor thermal stability thereof, and the resultant laurolactam is unsatisfactory due to the low quality thereof. However, the prior art does not teach or suggest any possible influence of oxygen atom-containing organic compounds having 12 carbon atoms and cycloaliphatic unsaturated hydrocarbon compounds having 12 carbon atoms, for example, carbonyl group-containing $C_{12}$-noncyclo-aliphatic and cycloaliphatic hydrocarbon compounds, epoxy group-containing $C_{12}$-noncyclo-aliphatic and cycloaliphatic hydrocarbon compounds, aldehyde group-containing $C_{12}$-noncyclo-aliphatic and cycloaliphatic hydrocarbon compounds, hydroxyl group-containing $C_{12}$-noncyclo-aliphatic and cycloaliphatic hydrocarbon compounds contained in the starting cyclododecanone material, on the quality of the target laurolactam.

SUMMARY OF THE INVENTION

An object of the present invention is to provide a process for producing laurolactam having high quality, from cyclododecanone, with a high efficiency.

The above-mentioned object can be attained by the process of the present invention for producing laurolactam from cyclododecanone, which comprises reacting cyclododecanone with a hydroxylamine salt of a mineral acid to prepare cyclododecanoneoxime, and converting the resultant cyclododecanoneoxime to laurolactam through the Beckmann rearrangement reaction, wherein a content of each of oxygen atom-containing organic compounds having 12 carbon atoms and cycloaliphatic unsaturated hydrocarbon compounds having 12 carbon atoms, each contained, as an impurity, in cyclododecanone used as a starting material, is controlled to 1,000 ppm or less.

In the process of the present invention for producing laurolactam, the total content of the oxygen atom-containing organic compounds having 12 carbon atoms and the cycloaliphatic unsaturated hydrocarbon compounds having 12 carbon atoms and respectively contained, as impurities, in the starting cyclododecanone material, is preferably controlled to 2,000 ppm or less.

In the process of the present invention for producing laurolactam, the oxygen atom-containing organic compounds having 12 carbon atoms and contained, as impurities, in the starting cyclododecanone material may include noncyclo-hydrocarbon compounds or cycloaliphatic hydrocarbon compounds respectively having at least one carbonyl group per molecule thereof.

In the process of the present invention, for producing laurolactam, the oxygen atom-containing organic compounds having 12 carbon atoms and contained, as impurities, in the starting cyclododecanone material may include noncyclo-hydrocarbon compounds or cycloaliphatic hydrocarbon compounds respectively having at least one epoxy group per molecule thereof.

In the process of the present invention for producing laurolactam, the oxygen atom-containing organic compounds having 12 carbon atoms and contained, as impurities, in the starting cyclododecanone material may include noncyclo-hydrocarbon compounds or cycloaliphatic hydrocarbon compounds respectively having at least one aldehyde group per molecule thereof.

In the process of the present invention for producing laurolactam, the oxygen atom-containing organic compounds having 12 carbon atoms and contained, as impurities, in the starting cyclododecanone material may include noncyclo-hydrocarbon compounds or cycloaliphatic hydrocarbon compounds respectively having at least one hydroxyl group per molecule thereof.

In the process of the present invention for producing laurolactam, the content of each of the oxygen atom-containing organic compounds having 12 carbon atoms and the cycloaliphatic unsaturated hydrocarbon compounds having 12 carbon atoms, and contained, as impurities, in the starting cyclododecanone material, is preferably controlled to 500 ppm or less.

In the process of the present invention for producing laurolactam, the starting cyclododecanone material is preferably pre-treated with an aqueous solution of an alkali metal hydroxide or toluenesulfonic acid at a temperature of 70 to 230° C.

In the process of the present invention for producing laurolactam, the starting cyclododecanone material is preferably pre-treated with a solid acid at a temperature of 70 to 230° C.

DESCRIPTION OF THE PREFERRED EMBODIMENTS

The inventors of the present invention conducted extensive researches concerning causes of degradation in quantity of the target laurolactam when produced from a starting cyclododecanone material, and found that when the starting cyclododecanone material contained at least one member selected from oxygen atom-containing organic compounds, usually oxygen atom-containing cycloaliphatic compounds, having 12 carbon atoms and cycloaliphatic unsaturated hydrocarbon compounds having 12 carbon atoms, as an impurity, in an amount more than a limited amount, the resultant laurolactam could not exhibit, even after a distillation refining is applied thereto, satisfactory quality, for example, a satisfactory differential light transmittance (which will be referred to as LT.diff, hereinafter) of 25% or less, preferably 15% or less. Also, the inventors of the present invention further found that the target laurolactam having satisfactory quality, for example, a LT.diff of 25% or less, preferably 15% or less could be obtained by controlling the content of each of oxygen atom-containing organic compounds having 12 carbon atoms and cycloaliphatic unsaturated hydrocarbon compounds having 12 carbon atoms, contained as impurities, in the starting cyclododecanone material to a specific value or less. The process of the present invention was completed on the basis of the above-mentioned findings.

In the process of the present invention, a starting cyclododecanone material is subjected to a reaction with a hydroxylamine salt of a mineral acid to prepare cyclododecanoneoxime, and then the resultant cyclododecanoneoxime is converted to laurolactam by the Beckmann rearrangement reaction.

The starting cyclododecanone material usable for the process of the present invention can be prepared by oxidizing cyclododecane with a molecular oxygen-containing gas or by isomerizing epoxycyclododecane. In the oxidation method, cyclododecane is oxidized with oxygen gas or a molecular oxygen-containing gas in the presence of a boron compound to provide a reaction product mixture comprising cyclododecanol and cyclododecanone, the reaction product mixture is hydrolysed, the boron compound is removed from the hydrolysis product mixture, non-reacted cyclododecane is separated and recovered from the hydrolysis product mixture by distillation, and a mixture of cyclododecanol with cyclododecanone is collected from the residual fraction. The mixture is subjected to a dehydrogenation procedure to convert cyclododecanol to cyclododecanone. In this dehydrogenation procedure, a portion of the resultant cyclododecanone is occasionally further dehydrogenated to produce cyclododecenone.

Also, in the oxidation of the starting cyclododecane material with a molecular oxygen-containing gas, cyclododecane is oxidized into cyclododecanone and occasionally the resultant cyclododecanone is further oxidized into $C_{12}$ 1,2-diketone compounds and $C_{12}$ α-hydroxyketone compounds and, further occasionally, the resultant $C_{12}$ α-hydroxyketone compounds are dehydrogenated to produce $C_{12}$ 1,2-diketone compounds (cyclododecane-1,2-dione) in the dehydrogenation procedure for cyclododecanole.

In the process for producing cyclododecanone from epoxycyclododecadiene by reducing epoxycyclododecadiene with hydrogen in the presence of a platinum group metal catalyst, and isomerizing the resultant epoxycyclododecane in the presence of an alkali metal salt, to produce the target cyclododecanone, if the reduction reaction of epoxycyclododecadiene with hydrogen is incompletely conducted, epoxycyclododecene having a non-hydrogenated double bond remains in the reaction product mixture. When the epoxycyclododecane material containing epoxycyclododecene is subjected to the isomerization reaction, the resultant cyclododecanone contains cyclododecenone.

The cyclododecenone contained, as an impurity in the target cyclododecanone, is very difficult to separate and remove from the target cyclododecanone by distillation or other refining procedures. Thus, the removal of cyclododecenone causes the cost of production of the target cyclododcanone to increase. Therefore, in the production of cyclododecanone, the conditions of the production must be carefully controlled so that the production of cyclododecenone is prevented.

Also, in the isomerization of epoxycyclododecane in the presence of an alkali metal salt for the production of the target cyclododecanone, occasionally, small amounts of cyclododecene, cyclododecadiene and cyclododecenol are produced as by-products. These by-product compounds can be separated and removed from cyclododecanone by distillation. However, the yield of the target cyclododecanone decreases with increase in degree of refining. Thus, an increase in refining degree causes an economical disadvantage in the production of the target compound. The refining degree of the target compound must be controlled in consideration of the desired quality of the target cyclododecanone and the production cost thereof.

In the process for producing cyclododecanone by reducing epoxycyclododecadiene with hydrogen in the presence of a platinum group metal catalyst and isomerizing the resultant epoxycyclododecane in the presence of an alkali metal salt, the by-product, $C_{12}$ 1,2-diketone compounds are not directly produced. However, in the case where cyclododecanone is handled in the presence of a molecular oxygen-containing gas at a temperature of 100° C. or more, $C_{12}$ 1,2-diketone compounds (cyclododecane-1,2-dione) are produced. As mentioned above, the production of the diketone compound must be carefully prevented by, for example, controlling the reaction conditions and/or the handling conditions.

Further, if the isomerization reaction of epoxycyclododecane is incompletely carried out, the non-isomerized epoxycyclododecane remains in the resultant reaction product.

As mentioned above, as the removal of the residual epoxycyclododecane from the target compound causes the resultant refined target compound to be costly, the reaction conditions for the production of the target cyclododecanone must be carefully controlled.

Further, in the isomerization of epoxycyclododecane, occasionally cycloundecanecarboxyaldehyde is produced as a by-product. The by-product cycloundecanecarboxyaldehyde is difficult to separate and remove from the target cyclododecanone by distillation, etc.

Accordingly, in the process of the present invention for producing laurolactam from a starting cyclododecanone material, it is essential that a content of each of oxygen atom-containing organic compounds, preferably oxygen atom-containing cycloaliphatic compounds, having 12 carbon atoms, and cycloaliphatic unsaturated hydrocarbon compounds having 12 carbon atoms, each contained, as an impurity, in the starting cyclododecanone material is controlled to 1,000 ppm or less, preferably 500 ppm or less, more preferably 300 ppm or less.

When the content of each impurity as mentioned above is controlled to 1,000 ppm or less, the resultant target laurolactam exhibits satisfactory quality, for example, a very low LT.diff.

The oxygen atom-containing $C_{12}$ organic compounds to be controlled in the process of the present invention include, $C_{12}$ non-cyclic aliphatic hydrocarbon compounds and $C_{12}$ cycloaliphatic hydrocarbon compounds, each containing at least one carbonyl group per molecule thereof, for example, cyclododecadienone, cyclododecenone, 1-hydroxycyclododecane-2-one, and cyclododecane-1,2-dione.

Also, the oxygen atom-containing $C_{12}$ organic compounds include non-cyclic aliphatic $C_{12}$ hydrocarbon compounds and cycloaliphatic $C_{12}$ hydrocarbon compounds each having at least one epoxy group per molecule thereof, for example, epoxycyclododecane, epoxycyclododecene, epoxycyclododecadiene, diepoxycyclododecane and diepoxycyclododecene.

Further, the oxygen atom-containing $C_{12}$ organic compounds include $C_{12}$ non-cyclic aliphatic hydrocarbon compounds and $C_{12}$ cycloaliphatic hydrocarbon compounds each having at least one aldehyde group per molecule thereof, for example, undecylaldehyde and cycloundecanecarboxyaldehyde.

Furthermore, the oxygen atom-containing $C_{12}$ organic compounds include non-cyclic aliphatic $C_{12}$ hydrocarbon compounds and cycloaliphatic $C_{12}$ hydrocarbon compounds each containing at least one hydroxyl group, for example n-dodecanol, cylododecanol, cyclododecenol, and 1-hydroxycyclododecane-2-one.

The $C_{12}$ cycloaliphatic unsaturated hydrocarbon compounds to be controlled in the process of the present invention are constituted from only carbon atoms and hydrogen atoms and include, for example, cyclododecene and cyclododecadiene.

When the starting cyclododecanone material contains two or more types of the above-mentioned impurities, the total content of the impurities is preferably controlled to 2,000 ppm or less, more preferably 1,800 ppm or less, still more preferably 1,500 ppm or less, furthermore preferably 1,000 ppm or less. If the total content of the impurities is more than 2,000 ppm, even when each of the contents of impurities is 1,000 ppm or less, the resultant laurolactam may exhibit an unsatisfactory quality.

The contents of the impurities, namely, the oxygen atom-containing $C_{12}$ organic compounds and the $C_{12}$ cycloaliphatic unsaturated hydrocarbon compounds, contained in the starting cyclododecanone material are controlled to the desired level by, for example, the following means.

To control the contents of the non-cyclic aliphatic or cycloaliphatic $C_{12}$ hydrocarbon compounds having at least one carbonyl group per molecule thereof, contained, as impurities in the starting cyclododecanone material each to 1,000 ppm or less, the reaction conditions for the isomerization of epoxycyclododecane are carefully controlled and/or the impurity-containing cyclododecanone material is brought into contact with an aqueous solution of an alkaline compound, for example, sodium hydroxide and heat-treated at a temperature of 70 to 230° C., preferably 100 to 200° C., while stirring the mixture, and then the resultant treatment product is refined by distillation.

To control the contents of the non-cyclic aliphatic and cycloaliphatic $C_{12}$ hydrocarbon compounds having at least one epoxy group per molecule thereof to 1,000 ppm or less, the reaction conditions for production of cyclododecanone is carefully controlled and/or the cyclododecanone material containing the impurities is heat-treated with at least one member selected from a solid acids, for example, γ-alumina and/or silica-alumina, and ion-exchange resins, at a temperature of 70 to 230° C., preferably 80 to 220° C.

To control the contents of the non-cyclic aliphatic and cycloaliphatic $C_{12}$ hydrocarbon compounds having at least one aldehyde group per molecule thereof to 1,000 ppm or less, the reaction conditions for the production of cyclododecanone are carefully controlled and/or the impurity-containing cyclododecanone material is heat-treated together with an alkaline substance, for example, sodium hydroxide or an acid substance, for example, toluenesulfonic acid, at a temperature of 70° C. or more, preferably 70 to 230° C., more preferably 80° C. to 220° C., and/or the impurity-containing cyclododecanone material is subjected to a reduction treatment with hydrogen in the presence of a Ru or Ni catalyst, and then the reduction-treated material is subjected to a precision distillation.

To control the contents of the non-cyclic aliphatic and cycloaliphatic $C_{12}$ hydrocarbon compounds having at least hydroxyl group per molecule thereof to 1,000 ppm or less, the reaction conditions for the production of cyclododecanone are carefully controlled and/or the impurity-containing cyclododecanone material is subjected to a precision distillation, and/or the impurity-containing cyclododecanone material is heat-treated in the presence of an acid substance, for example, toluenesulfonic acid at a temperature of 70° C. or more, preferably 70 to 230° C., more preferably 80 to 220° C.

To control the contents of the aliphatic unsaturated $C_{12}$ hydrocarbon compounds to 1,000 ppm or less, the reaction conditions for the production of cyclododecanone are carefully controlled and/or the impurity-containing cyclododecanone material is subjected to a precision distillation.

In the case where the cyclododecanone material contains two or more types of impurities, preferably two or more of the above mentioned refining procedures are applied. However, sometimes, the contents of two or more impurities can be reduced by a single refining procedure.

The impurity content-controlled starting cyclododecanone material is reacted with a hydroxylamine salt of a mineral acid to provide cyclododecanoneoxime. The mineral acid is preferably selected from sulfuric acid and hydrochloric acid. The oxime-producing reaction is preferably carried out at a temperature of 70 to 110° C., more preferably 90 to 100° C. Also, the pH of the reaction mixture is preferably controlled to 1 to 10, more preferably 4 to 10, by using an aqueous alkaline solution, preferably an aqueous ammonia solution.

A solution of the resultant cyclododecanoneoxime is subjected to the Beckmann rearrangement reaction to prepare laurolactam. Preferably the Beckmann rearrangement reaction is carried out by heating the aqueous cyclododecanoneoxime solution in the presence of fuming sulfuric acid at a temperature of 90 to 130° C., more preferably 90 to 110° C. Cyclododecanoneoxime is in the state of a solid at room temperature and has a melting temperature of 135° C. This compound is very unstable at the melting temperature or higher. Thus, usually cyclododecanoneoxime in the state of a solution in a solvent is subjected to the Beckmann rearrangement reaction at the above-mentioned temperature. The solvent is preferably selected from cycloaliphatic hydrocarbons, for example, cyclododecane and isopropylcyclohexane; and alkanoneoximes, for example, cyclohexanoneoximes. After the reaction, the resultant reaction mixture is neutralized with an aqueous ammonia solution, and refined by a conventional refining procedure, for example, extraction or distillation, to collect refined laurolactam.

EXAMPLES

The present invention will be further explained in detail by the following examples.

In the examples and comparative examples, the differential light transmittance (LT.diff) of laurolactam was determined by the following measurement.

Measurement of LT.diff

A 2% by mass methyl alcohol solution of a sample of laurolactam to be tested in an amount of 100 ml was mixed with 10 ml of 0.1N aqueous potassium permanganate solution at a temperature of 20° C. and, 200 seconds after mixing, the resultant mixed liquid was placed in a 5 mm cell, and 240 second after mixing, a light transmittance (%) at a wavelength of 410 mm, of the mixed solution was measured. The resultant data is referred as to T1. In this measurement, as a reference liquid, a mixture liquid of 100 ml of a 2% by mass laurolactam solution in methyl alcohol with 20 ml of methyl alcohol was employed.

Then, 100 ml of methyl alcohol was mixed with 10 ml of a 0.01N aqueous potassium permanganate solution and, 200 seconds after mixing, the resultant mixed solution was placed in a 5 mm cell, and 240 seconds after mixing, the light transmittance (%), T2, of the mixed liquid at a wavelength of 410 mm was measured. In this measurement, as a reference liquid, distilled water was employed.

The LT.diff of the sample was calculated in accordance with the following equation;

$$LT.diff\ (\%)=T1-T2.$$

Example 1

In a SUS reactor having a capacity of 140 liters, 77 kg of a 15 mass % aqueous hydroxylamine sulfate solution were placed; a 25 mass % aqueous ammonia solution was mixed thereinto to an extent such that the pH of the mixture is adjusted to 5.5, while the temperature of the mixture is maintained at 60° C. or less; then 10 kg of cyclododecanone-oxime was further mixed with the pH-adjusted mixture and the temperature of the resultant mixture was adjusted to 90° C. Into the mixture, 9.5 kg of a starting cyclododecanone material consisting of cyclododecanone containing, as an impurity, 150 ppm of cyclododecenone were mixed, and a 25 mass % aqueous ammonia solution was further mixed therewith to control the pH and temperature of the resultant reaction mixture to 5.5 and 95° C., respectively. The reaction mixture was subjected to a reaction at the above-mentioned temperature for 4 hours, then left to stand for 0.5 hour to allow the reaction mixture is separated into an aqueous phase layer and a non-aqueous (organic) phase layer. The aqueous phase layer was withdrawn from an outlet located in the bottom of the reactor.

Then, the remaining organic phase fraction comprising cyclododecanoneoxime was withdrawn from the reactor, and the withdrawn organic phase fraction was fed in a feed rate of 3.6 kg/hr together with a mixture of 13 parts by mass of fuming sulfonic acid with 9 parts by mass of concentrated sulfuric acid, in a feed rate of 4 kg/hr, into a Beckmann rearrangement reaction vessel having a capacity of 10 liters. The temperature of the mixture in the reaction vessel was maintained at 90 to 100° C., and the residence time of the mixture in the reaction vessel was controlled to one hour. The resultant reaction mixture was withdrawn from the reaction vessel by overflowing, and fed at a feed rate of 7.6 kg/hr into a neutralization vessel containing saturated aqueous ammonium sulfate solution, and a 14 mass % aqueous ammonia solution was fed into the vessel to control the pH of the mixture in the vessel to 5.5. From the resultant reaction mixture, an organic phase fraction was separated and collected; the collected organic phase fraction was subjected to an extraction with toluene; and the resultant toluene extract was washed with water and then distilled under a reduced pressure of 0.2 kPa. As a distillate, refined laurolactam was collected.

The resultant refined laurolactam exhibited a LT.diff of 5.4%.

Example 2

A refined laurolactam was prepared by the same procedures as in Example 1, except that the starting cyclododecanone material consisted of cyclododecanone containing, as an impurity, 30 ppm of cyclododecane-1,2-dione.

The resultant refined laurolactam exhibited an LT.diff of 5.2%.

Example 3

A refined laurolactam was prepared by the same procedures as in Example 1, except that the starting cyclododecanone material consisted of cyclododecanone containing, as an impurity, 50 ppm of epoxycyclododecane.

The resultant refined laurolactam exhibited an LT.diff of 5.6%.

Example 4

A refined laurolactam was prepared by the same procedures as in Example 1, except that the starting cyclododecanone material consisted of cyclododecanone containing, 510 ppm of impurities comprising 160 ppm of cyclododecadiene, 150 ppm of cyclododecenone and 200 ppm of cyclododecenol.

The resultant refined laurolactam exhibited an LT.diff of 5.4%.

Example 5

A refined laurolactam was prepared by the same procedures as in Example 1, except that the starting cyclododecanone material consisted of cyclododecanone containing, as an impurity, 250 ppm of cycloundecanecarboxyaldehyde.

The resultant refined laurolactam exhibited n LT.diff of 6.2%.

Example 6

A refined laurolactam was prepared by the same procedures as in Example 1, except that the starting cyclododecanone material consisted of cyclododecanone containing 1,500 ppm of impurities comprising 700 ppm of cyclododecenone and 800 ppm of cycloaliphatic unsaturated hydrocarbon compounds having 12 carbon atoms.

The resultant refined laurolactam exhibited an LT.diff of 17.4%.

Comparative Example 1

A refined laurolactam was prepared by the same procedures as in Example 1, except that the starting cyclododecanone material consisted of cyclododecanone containing, as an impurity, 1,500 ppm of epoxycyclododecane.

The resultant refined laurolactam exhibited an LT.diff of 27.2%.

Comparative Example 2

A refined laurolactam was prepared by the same procedures as in Example 1, except that the starting cyclododecanone material consisted of cyclododecanone containing, as impurities, 900 ppm of cyclododecenone and 1,500 ppm of cyclocyclic unsaturated hydrocarbon compounds having 12 carbon atoms.

The resultant refined laurolactam exhibited an LT.diff of 28.2%.

Comparative Example 3

A refined laurolactam was prepared by the same procedures as in Example 1, except that the starting cyclododecanone material consisted of cyclododecanone containing, as an impurity, 1,500 ppm of cycloundecanecarboxyaldehyde.

The resultant refined laurolactam exhibited an LT.diff of 28.8%.

Comparative Example 4

A refined laurolactam was prepared by the same procedures as in Example 1, except that the starting cyclododecanone material consisted of cyclododecanone containing 2900 ppm of impurities comprising oxygen atom-containing cycloaliphatic compounds having 12 carbon atoms (including 700 ppm of cyclododecenone, 100 ppm of epoxycyclododecane, 500 ppm of cyclododecenol, 150 ppm of cyclododecanol and 1,100 ppm of cycloundecanecarboxyaldehyde) and 350 ppm of cyclododecadiene, as a cycloaliphatic unsaturated hydrocarbon compounds having 12 carbon atoms.

The resultant refined laurolactam exhibited an LT.diff of 29.5%.

Table 1 shows types and contents of the impurities in the starting cyclododecanone material and the LT.diff of the resultant refined laurolactam of Examples 1 to 6 and comparative Examples 1 to 4.

TABLE 1

| | The starting cyclododecanone material Impurities | | Differential light |
|---|---|---|---|
| Example No. | Type | Content (ppm) | transmittance (%) |
| Example | | | |
| 1 | Cyclododecenone | 150 | 5.4 |
| 2 | Cyclododecane-1,2-dione | 30 | 5.2 |
| 3 | Epoxycyclododecane | 50 | 5.6 |
| 4 | Cyclododecadiene | 160 | |
| | Cyclododecenone | 150 | |
| | Cyclododecenol | 200 | 5.4 |
| 5 | Cycloundecanecarboxyaldehyde | 250 | 6.2 |
| 6 | Cyclododecenone | 700 | |
| | $C_{12}$-Cycloaliphatic unsaturated hydrocarbon compounds | 800 | 17.4 |
| Comparative Example | | | |
| 1 | Epoxycyclododecane | 1500 | 27.2 |
| 2 | Cyclododecenone | 900 | |
| | $C_{12}$-Cycloaliphatic unsaturated hydrocarbon compounds | 1500 | 28.2 |
| 3 | Cycloundecanecarboxyaldehyde | 1500 | 28.8 |
| 4 | Cyclododecenone | 700 | |
| | Epoxycyclododecane | 100 | |
| | Cyclododecenol | 500 | |
| | Cyclododecanol | 150 | |
| | Cycloundecanecarboxyaldehyde | 1100 | |
| | Cyclododecadiene | 350 | 29.5 |

Example 7

A refined laurolactam was prepared by the same procedures as in Example 1, except that the starting cyclododecanone material was prepared by pre-treating a unrefined cyclododecanone material containing 700 ppm of cyclododecenone with an aqueous solution of 10% by mass of sodium hydroxide at 200° C. for 5 hours, and then subjecting the resultant pretreatment reaction mixture to refining distillation. In the pretreated cyclododecanone material, the content of cyclododecenone was 80 ppm.

The resultant refined laurolactam exhibited an LT.diff of 5.3%.

Example 8

A refined laurolactam was prepared by the same procedures as in Example 3, except that the starting cyclododecanone material was prepared by pre-treating a unrefined cyclododecanone material containing 2,800 ppm of epoxycylcododecane with γ-alumina at 200° C. for 2 hours, and subjecting the resultant pretreatment reaction mixture to refining distillation. In the pretreated cyclododecanone material, the content of epoxycylcododecane was 170 ppm.

The resultant refined laurolactam exhibited an LT.diff of 5.8%.

Example 9

A refined laurolactam was prepared by the same procedures as in Example 5, except that the starting cyclododecanone material was prepared by pre-treating a unrefined cyclododecanone material containing 1,500 ppm of cycloundecanecarboxyaldehyde with an aqueous solution of 10% by mass of sodium hydroxide at 180° C. for 10 hours, and subjecting the resultant pretreatment reaction mixture to refining distillation. In the pretreated cyclododecanone material, the content of cycloundecanecarboxyaldehyde was not detected.

The resultant refined laurolactam exhibited an LT.diff of 5.0%.

Example 10

A refined laurolactam was prepared by the same procedures as in Example 4, except that the starting cyclododecanone material was prepared by pre-treating a unrefined cyclododecanone material containing 3,200 ppm of cyclododecenol with toluenesulfonic acid at 220° C. for one hour, and subjecting the resultant pretreatment reaction mixture to precision distillation. In the pretreated cyclododecanone material, the content of cyclododecenol was 80 ppm.

The resultant refined laurolactam exhibited an LT.diff of 5.4%.

Laurolactam having high quality can be produced with high efficiency and stability by the process of the present invention in which the content of each of oxygen atom-containing organic compounds having 12 carbon atoms and cycloaliphatic unsaturated hydrocarbon compounds having 12 carbon atoms, contained in the starting cyclododecanone material is controlled to 1,000 ppm or less.

What is claimed is:

1. A process for producing laurolactam from cyclododecanone, comprising reacting cyclododecanone with a hydroxylamine salt of a mineral acid to prepare cyclododecanoneoxime, and converting the resultant cyclododecanoneoxime to laurolactam through the Beckmann rearrangement reaction,
wherein a content of each of the oxygen atom-containing organic compounds having 12 carbon atoms and cycloaliphatic unsaturated hydrocarbon compounds having 12 carbon atoms, contained, as an impurity, in the cyclododecanone used as a starting material, is controlled to 1,000 ppm or less.

2. The process for producing laurolactam as claimed in claim 1, wherein the total content of the oxygen atom-containing organic compounds having 12 carbon atoms and the cycloaliphatic unsaturated hydrocarbon compounds having 12 carbon atoms and respectively contained, as impurities, in the starting cyclododecanone material, is controlled to 2,000 ppm or less.

3. The process for producing laurolactam as claimed in claim 1 or 2, wherein the oxygen atom-containing organic compounds having 12 carbon atoms and contained, as impurities, in the starting cyclododecanone material include noncyclo-aliphatic hydrocarbon compounds and cycloaliphatic hydrocarbon compounds respectively having at least one carbonyl group per molecule thereof.

4. The process for producing laurolactam as claimed in claim 1 or 2, wherein the oxygen atom-containing organic compounds having 12 carbon atoms and contained, as impurities, in the starting cyclododecanone material include noncyclo-aliphatic hydrocarbon compounds and cycloaliphatic hydrocarbon compounds respectively having at least one epoxy group per molecule thereof.

5. The process for producing laurolactam as claimed in claim 1 or 2, wherein the oxygen atom-containing organic compounds having 12 carbon atoms and contained, as impurities, in the starting cyclododecanone material include noncyclo-aliphatic hydrocarbon compounds and cycloaliphatic hydrocarbon compounds respectively having at least one aldehyde group per molecule thereof.

6. The process for producing laurolactam as claimed in claim 1 or 2, wherein the oxygen atom-containing organic compounds having 12 carbon atoms and contained, as impurities, in the starting cyclododecanone material include noncyclo-aliphatic hydrocarbon compounds and cycloaliphatic hydrocarbon compounds respectively having at least one hydroxyl group per molecule thereof.

7. The process for producing laurolactam as claimed in claim 1, wherein a content of each of the oxygen atom-containing organic compounds having 12 carbon atoms and the cycloaliphatic unsaturated hydrocarbon compounds having 12 carbon atoms, and contained, as impurities, in the starting cyclododecanone material, is controlled to 500 ppm or less.

8. The process for producing laurolactam as claimed in claim 1, wherein the starting cyclododecanone material is pre-treated with an alkali metal hydroxide or toluenesulfonic acid at a temperature of 70 to 230° C.

9. The process for producing laurolactam as claimed in claim 1, wherein the starting cyclododecanone material is pre-treated with at least one member selected from solid acids and ion-exchange resins at a temperature of 70 to 230° C.

* * * * *